United States Patent [19]

Rich

[11] Patent Number: 4,780,501
[45] Date of Patent: Oct. 25, 1988

[54] IMIDOPOLYSILOXANES AND METHOD FOR MAKING

[75] Inventor: Jonathan D. Rich, Rexford, N.Y.

[73] Assignee: General Electric Company, Schenectady, N.Y.

[21] Appl. No.: 164,767

[22] Filed: Mar. 7, 1988

Related U.S. Application Data

[63] Continuation-in-part of Ser. No. 902,814, Sep. 2, 1986, abandoned.

[51] Int. Cl.$^4$ ............................................. C08L 83/04
[52] U.S. Cl. ..................................... 524/860; 528/24; 528/26; 528/27; 548/406; 525/474
[58] Field of Search .................. 524/860; 528/24, 27, 528/26; 548/406; 525/474

[56] References Cited

U.S. PATENT DOCUMENTS

| | | | |
|---|---|---|---|
| 4,472,565 | 9/1984 | Ryang | 528/26 |
| 4,522,985 | 6/1985 | Ryang | 528/26 |
| 4,595,732 | 6/1986 | Ryang | 528/26 |

OTHER PUBLICATIONS

J. R. Pratt et al., Journal of Organic Chemistry, vol. 38, No. 25 (1973), pp. 4271–4274.

Primary Examiner—John C. Bleutge
Assistant Examiner—Ralph H. Dean, Jr.
Attorney, Agent, or Firm—William A. Teoli; James C. Davis, Jr.; James Magee, Jr.

[57] ABSTRACT

Imidopolysiloxane gums, resins and fluids are made by equilibrating imidocylclopolysiloxanes with organocyclopolysiloxanes, or cohydrolyzing imidosilanes and organosilanes. The resulting imidopolysiloxanes are useful as temperature and solvent resistant resin and fluids and can be converted to temperature and solvent resistant elastomers.

7 Claims, No Drawings

IMIDOPOLYSILOXANES AND METHOD FOR MAKING

CROSS REFERENCE TO RELATED APPLICATIONS

This application is a continuation-in-part of copending application Ser. No. 902,814, filed Sept. 2, 1986 now abandoned. Reference is also made to copending application Ser. No. 765,089, filed Aug. 13, 1985 for SILYLATION METHOD AND SILANES MADE THEREFROM, now U.S. Pat. No. 4,709,054.

BACKGROUND OF THE INVENTION

In copending application Ser. No. 902,813, filed Sept. 2, 1986, now U.S. Pat. No. 4,730,055, which is a continuation-in-part of copending application Ser. No. 647,301, filed Aug. 30, 1984, for METHOD FOR SILYLATING AROMATIC IMIDES AND IMIDES MADE THEREFROM, now abandoned, various silyl imides are shown having nuclear-bound silicon atoms attached to aromatic imide radicals by silicon carbon linkages. These silyl imides can be synthesized by the use of a polysilane, such as dimethoxytetramethyldisilane and an effective amount of a transition metal catalyst, for example palladium. These reactants are used in combination with haloaromatic imide, for example, N-butyl-4-chlorophthalimide. In addition to various imidosilanes, 1,3-bisimidotetraorganodisiloxanes were also synthesized.

I have now found that a wide variety of imidopolysiloxanes also can be made by equilibrating the above-mentioned 1,3-bisimidotetraorganodisiloxane with cyclic organosiloxane, or cohydrolyzing imidoalkoxysilane with organoalkoxysilane, or imidohalosilane with organohalosilanes. In addition to equilibrating imidotetraorganodisiloxane with cyclic organosiloxane, there can be equilibrated imidocyclic siloxane with cyclic organosiloxane.

The imidopolysiloxanes which can be made in accordance with the practice of the present invention have an imide to silicon ratio of at least 0.01, and comprise at least three chemically combined units included within the formula,

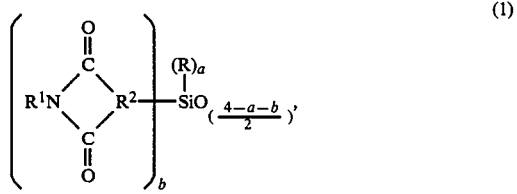

(1)

where R and $R^1$ are selected from $C_{(1-14)}$ monovalent hydrocarbon radicals and $C_{(1-14)}$ monovalent hydrocarbon radicals substituted with neutral radicals, $R^2$ is selected from $C_{(6-14)}$ trivalent aromatic hydrocarbon radicals and $C_{(6-14)}$ trivalent aromatic hydrocarbon radicals substituted with neutral radicals, a and b are whole numbers equal to 0 to 3 inclusive, and the sum of a+b has an average value of from about 1 to about 2.67 inclusive.

STATEMENT OF THE INVENTION

There is provided by the present invention, imidopolysiloxanes having an imide to silicon ratio of at least 0.01 which comprise at least three chemically combined siloxy units as shown by Formula 1.

There are included by R of Formula 1, $C_{(1-8)}$ alkyl radicals such as methyl, ethyl, propyl, butyl, pentyl, hexyl; haloalkyl radicals such as chloroethyl, trifluoropropyl; cyanoalkyl radicals such as cyanoethyl, cyanopropyl; aryl radicals, for example phenyl, tolyl, xylyl, naphthyl, anthryl; haloaryl such as chlorophenyl, bromotolyl; nitroaryl such as nitrophenyl, nitrotolyl. R in Formula 1 can be all the same radical or a mixture of two or more of the aforementioned radicals. Radicals included by $R^1$ are alkyl radicals and aryl radicals, included by R. Radicals included by $R^2$ are, for example,

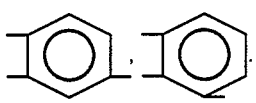

Included within the imidosiloxanes of Formula 1, there are imidosiloxane resins having an imide to silicon ratio of at least 0.01 having the formula,

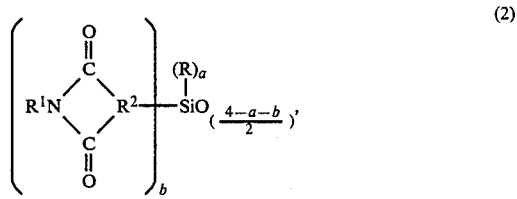

(2)

where R, $R^1$, $R^2$, a and b are as previously defined and the sum of a+b is equal to about 1 to about 1.5 inclusive.

The imidosiloxanes of Formula (3) can be made by hydrolyzing imidosilanes of the formula,

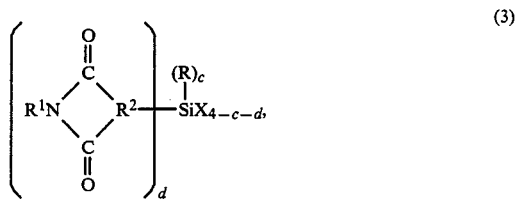

(3)

or cohydrolyzing such imidosilanes with organosilanes of the formula,

(4)

where R, $R^1$ and $R^2$ are as previously defined, X is a hydrolyzable radical selected from halogen, $C_{(1-8)}$ alkoxy or $C_{(6-14)}$ aryloxy, c is a whole number equal to 0 to 2 inclusive, d is a whole number equal to 1 to 3 inclusive, and the sum of c+d is equal to about 1 to 3 inclusive, e is a whole number equal to 0 to 3 inclusive, and the sum of c+d+e is equal to 1 to 2.67 inclusive.

Some of the imidosilanes included by Formula (3) are, for example, N-methyl-4-chlorodimethylsilylphthalimide, N-methyl-4-dichloromethylsilylphthalimide, N-methyl-4-trichlorosilylphthalimide, N-ethyl-4-chlorodimethylsilylphthalimide; N-phenyl-4-chlorodimethylsilylphthalimide, N-phenyl-4-dichloromethylsilylphthalimide, N-methyl-4-methoxydimethylsilylphthalimide, and N-methyl-4-dimethoxysilylphthalimide.

Among the organosilanes shown by Formula (4), there are included dimethyldichlorosilane, dimethyldimethoxysilane, phenylmethyldichlorosilane, phenylethyldimethoxysilane, diphenyldichlorosilane, diphenyldimethoxysilane, methyltrichlorosilane, and methyltrimethoxysilane.

In addition to the above-described imidopolysiloxane resins which exhibit superior solvent resistance and temperature stability, there are also included in the scope of Formula 1, solvent resistant and temperature resistant fluids having an imide to silicon ratio of at least 0.01 and a viscosity of less than about 100,000 centipoises at 25° C. of the formula,

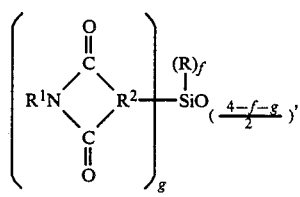
(5)

where R, R¹, and R² are as previously defined, f has a value of from 0 to 3 inclusive, g has a value of from 0 to 3 inclusive, or 1 to 3 inclusive, and the sum of f and g has a value of about 1.95 to 2.01 inclusive. The imidopolysiloxane fluids of the present invention are solvent resistant and heat stable as compared to conventional organopolysiloxane fluids. These heat stable fluids also can be made by cohydrolyzing silanes of formulas (3) and (4).

Also included within the imidopolysiloxanes of formula (5) are imidopolysiloxane gums having an imide to silicon ratio of at least 0.01, and a viscosity of from about $10^5$ to $10^8$ centipoises. These gums also can be made by cohydrolyzing silanes of formulas (3) and (4). They can be converted to high strength elastomers when reinforced with from about 50 to 500 parts of reinforcing filler per 100 parts of gum. Suitable reinforcing fillers are, for example, fume silica, and precipitated silica. Suitable curing catalysts which can be used to convert the imidosiloxane gums of the present invention to the elastomeric state are, for example, benzoylperoxide and dicumylperoxide which can be employed at from 0.01 to 10 parts of curing catalysts per 100 parts of gum. It is preferred to utilize sufficient organosilane or cyclicsiloxane having chemically combined alkenyl radicals such as vinyl attached to silicon, for example methylvinyltetrasiloxane to provide a ratio of about 0.01 to 2 moles of vinyl, per silicon atom, in the imidopolysiloxane gum to achieve optimum elastomeric properties.

There is also included by the present invention, imidocyclopolysiloxane having the formula,

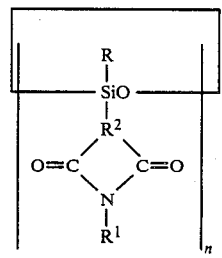
(6)

where R, R¹ and R² are as previously defined, and n is an integer having a value of from 3 to 16 inclusive. Some of the imidocyclopolysiloxanes included within Formula (6) are, for example:
tri-N-methylphthalimidyl-trimethylcyclotrisiloxane,
tetra-N-methylphthalimidyl-tetramethylcyclotetrasiloxane,
penta-N-methylphthalimidyl-pentamethylcyclopentasiloxane,
hexa-N-methylphthalimidyl-hexamethylcyclohexasiloxane;
tri-N-ethylphthalimidyl-trimethylcyclotrisiloxane,
tetra-N-ethylphthalimidyl-tetramethylcyclotetrasiloxane,
tri-N-propylphthalimidyl-trimethylcyclotrisiloxane,
tetra-N-propylphthalimidyl-tetamethylcyclotetrasiloxane,
tri-N-butylphthalimidyl-trimethylcyclotrisiloxane,
tetra-N-butylphthalimidyltetramethylcyclotetrasiloxane,
tri-N-phenylphthalimidyl-trimethylcyclotrisiloxane, and
tetra-N-phenylphthalimidyl-tetramethylcyclotetrasiloxane.

In order that those skilled in the art will be better able to practice the invention, the following examples are given by way of illustration and not by way of limitation. All parts are by weight.

EXAMPLE 1

A reaction mixture containing 4.1 gm (0.021 moles) of N-methyl-4-chlorophthalimide and 4.8 gm (0.021 moles) of sym-tetrachlorodimethyldisilane in o-xylene solvent is heated to reflux temperature for 24 hours in the presence of 1 mole % palladium on silica catalyst. Vacuum distillation at 168°/0.1 torr provides N-methyl-4-dichloromethylsilylphthalimide. It is a white crystalline solid, m.p. 89°–94° C. nmr(CCl₄, CH₂Cl₂ ref) δ 8.16 (S, 1H, Arom H₃) δ 8.05 (d, 1 J-10 Hz, Arom H₆) δ 7.78 (d. 1H, J-10 Hz, Arom H₅) δ 3.11 (S, 3H, N—CH₃) δ 1.07 (S, 3H, Si—CH₃) mass spec calc. 272.9779 obs. 272.9776.

There was added 0.11 ml of water to a 50 ml solution of equal parts of acetone and tetrahydrofuran containing 2.0 grams (7.3 ml) of N-methyl-4-dichloromethylsilylphthalimide. The resulting solution was stirred at room temperature for two hours. The mixture was then poured into an excess of water and was extracted with ether. The ether was washed, removed and dried with magnesium sulfite. Filtration and removal of the ether solvent gave 1.55 grams or a 97% yield of N-methyl-4-phthalimido-methylcyclosiloxane as a glassy solid. Liquid chromatographic analysis further confirmed the formation of phthalimidocyclopolysiloxane having an average of 3–15 chemically combined phthalimedo methylsiloxy units. Its identity was further confirmed by mass spectral analysis.

EXAMPLE 2

A 50 ml solution containing 1.4 grams of octamethylcyclotetrasiloxane and 1.4 grams of N-methyl-4-phthalimidocyclomethylsiloxane was heated to 80° C.

Hexamethyldisiloxane (6.4 milligrams) was added as a chain stopper. There was then added to this solution, a catalytic amount of Nafion acidic resin catalyst. The mixture was heated with stirring at 80° C. for 15 hours.

There was obtained a 2.1 gram (75% yield) of product upon filtering the mixture to remove the catalyst and distilling the toluene solvent. Based on method of preparation, the product was a imidopolysiloxane copolymer consisting of chemically combined dimethylsiloxy units and N-methyl-4-phthalimido methylsiloxy units having trimethysiloxy end groups. The copolymer was found to be a tough thermoplastic silicone elastomer having good solvent resistance to hydrocarbon liquids. The identity of the copolymer was further confirmed by its NMR spectra.

EXAMPLE 3

An excess of water was added to equal part solution of tetrahydrofuran in acetone containing 2.75 grams (10 millimole) of N-methyl-4-dichloromethylsilylphthalimide and 1.29 grams of dimethyldichlorosilane. The mixture was stirred at room temperature for two hours. An imidopolysiloxane was obtained which was extracted from water with ether, dried and the ether removed in vacuo to give 20 grams (68% yield) of an oligomeric siloxane consisting of chemically combined dimethylsiloxy units and N-methyl-4-phthalimidomethylsiloxy units.

The material was heated to 80° C. in 25 ml of dried toluene with 6 microliters (0.028 millimole) of hexamethyldisiloxane as a chain terminator. Catalytic amount of Nafion resin was introduced and the mixture heated at 80° C. for 15 hours. Filtration of the catalyst and removal of the solvent in vacuo provided 2.9 grams (89% yield) of a trimethylsiloxy terminated copolymer of chemically combined dimethylsiloxy units and N-methyl-4-phthalimidopolymethylsiloxy units having trimethylsiloxy chain stopper.

Although the above examples are directed to only a few of the very many variables which can be utilized in the practice of the method of the present invention, it should be understood that the method of the present invention involves the use of a much broader variety of organohalosilanes and imidosilanes or cyclicpolysiloxane obtained from the aforementioned halosilanes by hydrolysis as shown in the description preceding these examples.

What is claimed and sought to be protected by Letters Patent of the United States is as follows:

1. Imidopolysiloxane having an imide to silicon ratio of at least 0.01 and comprising at least three chemically combined siloxy units of the formula,

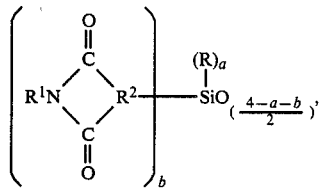

where R and $R^1$ are selected from the group consisting of $C_{(1-14)}$ monovalent hydrocarbon radicals and $C_{(1-14)}$ monovalent radicals selected from the class consisting of haloalkyl, cyanoalkyl, haloaryl, and nitroaryl, $R^2$ is selected from $C_{(6-14)}$ trivalent aromatic hydrocarbon radicals, a and b are whole numbers equal to 0 to 3 inclusive, and the sum of a+b has an average value of from about 1 to about 2.67, inclusive.

2. The imidopolysiloxane of claim 1, wherein the imidopolysiloxane is a resin.

3. The imidopolysiloxane of claim 1, wherein the imidopolysiloxane is a fluid.

4. The imidopolysiloxane of claim 1, wherein the imidopolysiloxane is a gum.

5. Imidocyclopolysiloxane having the formula,

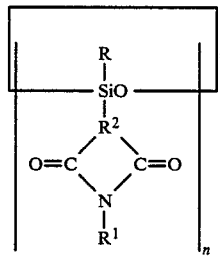

where R and $R^1$ are selected from $C_{(1-14)}$ monovalent hydrocarbon radicals and $C_{(1-14)}$ monovalent radicals selected from the class consisting of haloalkyl, cyanoalkyl, haloaryl and nitroaryl, $R^2$ is selected from $C_{(6-14)}$ trivalent aromatic hydrocarbon radicals, and n is an integer having a value of from 3 to 16, inclusive.

6. A heat curable silicone composition comprising by weight,
(1) 100 parts of a silicone imidopolysioxane gum having an imide to silicon ratio of at least 0.01, and consisting essentially of chemically combined units of the formula,

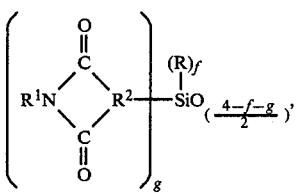

(2) 50 to 500 parts of filler, and
(3) an effective amount of a peroxide curing catalyst, where R and $R^1$ are selected from the group consisting of $C_{(1-14)}$ monovalent hydrocarbon radicals and $C_{(1-14)}$ monovalent radicals selected from the class consisting of haloalkyl, cyanoalkyl, haloaryl, and nitroaryl, $R^2$ is selected from the group consisting of $C_{(6-14)}$ trivalent aromatic hydrocarbon radicals, f has a value of from 0 to 3 inclusive, g has a value of from 0 to 3 inclusive, and the sum of f and g has a value of about 1.95 to 2.01, inclusive.

7. A heat curable silicone composition in accordance with claim 6, where the silicone imidopolysiloxane gum is an imidopolydimethylsiloxane having at least 0.01 mole of vinyl, per silicon atom.

* * * * *